(12) United States Patent
Makridakis

(10) Patent No.: US 9,555,016 B2
(45) Date of Patent: Jan. 31, 2017

(54) LYTIC AGENTS FOR USE IN TREATING INTRAVASCULAR CLOTS

(71) Applicant: COVIDIEN LP, Mansfield, MA (US)

(72) Inventor: Jennifer Makridakis, Mendon, MA (US)

(73) Assignee: Covidien LP, Mansfield, MA (US)

( * ) Notice: Subject to any disclaimer, the term of this patent is extended or adjusted under 35 U.S.C. 154(b) by 754 days.

(21) Appl. No.: 13/914,153

(22) Filed: Jun. 10, 2013

(65) Prior Publication Data
US 2014/0364505 A1    Dec. 11, 2014

(51) Int. Cl.
| A61K 31/155 | (2006.01) |
| A61K 9/00 | (2006.01) |
| A61K 47/02 | (2006.01) |
| A61K 9/08 | (2006.01) |

(52) U.S. Cl.
CPC .......... *A61K 31/155* (2013.01); *A61K 9/0019* (2013.01); *A61K 9/08* (2013.01); *A61K 47/02* (2013.01)

(58) Field of Classification Search
CPC .................................................. A61K 31/155
USPC ....................................................... 514/634
See application file for complete search history.

(56) References Cited

U.S. PATENT DOCUMENTS

| 5,610,308 A | 3/1997 | Real et al. |
| 6,638,931 B1 | 10/2003 | Tomczuk et al. |
| 2003/0078517 A1 | 4/2003 | Kensey |
| 2004/0259162 A1 | 12/2004 | Kappel et al. |

FOREIGN PATENT DOCUMENTS

| CN | 102417905 A * | 4/2012 |
| KR | 100486179 B1 | 4/2005 |

OTHER PUBLICATIONS

The English-translation of CN 102417905 A (Wu et al.) 2012.*
Knight, et al., "In vitro formation by reverse dialysis of collagen gels containing highly oriented arrays of fibrils," J. Biomed. Mater. Res., 41, 185-191 (1998).
Luo et al., "Creation of Fibrinogen-Enhanced Experimental Blood Clots to Evaluate Mechanical Thrombectomy Devices for Treatment of Acute Stroke: An In Vitro Study," J. Vasc. Interv. Radiol. Aug. 2012; 23(8): 1077-83.

* cited by examiner

*Primary Examiner* — Kevin E Weddington

(57) ABSTRACT

Agents and methods are provided for breaking down and/or assisting in the removal of clots, in embodiments chronic clots, from the vasculature. In embodiments, the agents and methods may be used in the vasculature, in particular the peripheral venous vasculature, in order to prevent clot formation and/or lyse clots in patients suffering from complications, such as thrombosis, or from conditions, such as deep vein thrombosis (DVT).

20 Claims, 3 Drawing Sheets

LYTIC AGENTS FOR USE IN TREATING INTRAVASCULAR CLOTS

TECHNICAL FIELD

The present disclosure relates to agents suitable for breaking down and or assisting in the removal of clots from the vasculature and, more particularly, to lytic agents suitable for use in treating intravascular clots.

BACKGROUND

Intravascular clots may form in a patient's vasculature for many reasons. For example, following various types of surgical procedures, as well as trauma, patients are prone to developing deep vein thrombosis (DVT). Patients suffering from hip, tibial and knee fractures undergoing orthopedic surgery, spinal cord injury, or stroke are especially at high risk.

Factors contributing to the development of intravascular clots, such as DVTs, include reduction of blood flow, vascular stasis, increase vessel wall contact time, coagulation changes, blood vessel damage, and pooling of blood in the lower extremities. It is believed that slowing of the blood flow or blood return system from the legs may be one of the main factors related to DVT with greatest effect during the intraoperative phase. Also of concern is the postoperative period. Even individuals immobilized during prolong travel on an airplane or automobile may be at risk.

Deep vein thrombosis may be systemically treated using anticoagulation drugs, catheter based thrombolysis, and/or thrombectomy procedures, with or without the use of a lytic agent. Catheter based thrombolysis is used predominantly to treat acute thrombosis (clot present <7-14 days), with thrombectomy indicated for removal of an acute to chronic thrombus (present >14 days), due to the increased formation of collagen within the clot. During treatment by thrombolysis, a tissue plasminogen activator (tPA), which is a clot specific thrombolytic, i.e., more effective in the resolution of acute clots by fibrinolysis than chronic clots, may be utilized. However, utilizing an agent like tPA is not suitable for all clots, including chronic clots.

Improved methods and agents for treating clots, including chronic clots, remain desirable.

SUMMARY

The present disclosure provides compositions for use in breaking down and or assisting in the removal of clots from the vasculature, as well as methods for preparing these compositions and methods for treating clots with these compositions.

In embodiments, methods of the present disclosure include identifying a clot in a patient's vasculature, and introducing to the clot a therapeutically effective amount of a lytic agent including at least one guanidine compound in a carrier, wherein the therapeutically effective amount of the at least one guanidine compound acts on the clot by slowing clot formation or enhancing clot dissolution.

In other embodiments, methods of the present disclosure include identifying a clot in a patient's vasculature, and introducing to the clot a therapeutically effective amount of a lytic agent including at least one guanidine compound such as guanidine hydrochloride, guanidine thiocyanate, guanidine isocyanate, tetramethylguanidinium iodide, and combinations thereof in a carrier, wherein the therapeutically effective amount of the at least one guanidine compound is present in the carrier composition at a molar concentration from about 0.5 M to about 6 M.

In yet other embodiments, methods of the present disclosure include identifying a clot in a patient's vasculature; and introducing to the clot a therapeutically effective amount of guanidine hydrochloride in a carrier selected from the group consisting of water, Hanks' Balanced Salt Solution, sodium chloride solutions, Phosphate Buffered Saline, Dulbecco's Modified Eagle's Medium, phosphate buffers, borate buffers, 1,3-Bis-[tris-(hydroxymethyl)-methyl-amino]-propane buffers, and combinations thereof, wherein the therapeutically effective amount of the at least one guanidine compound is present in the carrier composition at a molar concentration from about 0.5 M to about 6 M.

Lytic agents of the present disclosure include, in embodiments, at least one guanidine compound and a carrier, wherein the guanidine compound is present in the carrier at a molar concentration from about 0.5 M to about 6 M.

In other embodiments, lytic agents of the present disclosure include at least one guanidine compound selected from the group consisting of guanidine hydrochloride, guanidine thiocyanate, guanidine isocyanate, tetramethylguanidinium iodide, and combinations thereof; and a carrier, wherein the guanidine compound is present in the carrier at a molar concentration from about 0.5 M to about 6 M.

In yet other embodiments, lytic agents of the present disclosure include guanidine hydrochloride; and a carrier selected from the group consisting of water, Hanks' Balanced Salt Solution, sodium chloride solutions, Phosphate Buffered Saline, Dulbecco's Modified Eagle's Medium, phosphate buffers, borate buffers, 1,3-Bis-[tris-(hydroxymethyl)-methyl-amino]-propane buffers, and combinations thereof, wherein the guanidine compound is present in the carrier at a molar concentration from about 0.5 M to about 6 M.

Methods for producing lytic agents and/or compositions in accordance with the present disclosure include, in embodiments, combining combining a carrier composition selected from the group consisting of water, Hanks' Balanced Salt Solution, sodium chloride solutions, Phosphate Buffered Saline, Dulbecco's Modified Eagle's Medium, phosphate buffers, borate buffers, 1,3-Bis-[tris-(hydroxymethyl)-methyl-amino]-propane buffers, and combinations thereof with a guanidine compound, wherein the guanidine compound is present in the carrier composition in amounts from about 59 mg/ml to about 355 mg/ml.

In other embodiments, methods for producing lytic agents and/or compositions in accordance with the present disclosure include combining a carrier composition selected from the group consisting of water, Hanks' Balanced Salt Solution, sodium chloride solutions, Phosphate Buffered Saline, Dulbecco's Modified Eagle's Medium, phosphate buffers, borate buffers, 1,3-Bis-[tris-(hydroxymethyl)-methyl-amino]-propane buffers, and combinations thereof, with a guanidine compound selected from the group consisting of guanidine hydrochloride, guanidine thiocyanate, guanidine isocyanate, tetramethylguanidinium iodide, and combinations thereof, wherein the guanidine compound is present in the carrier composition in amounts from about 59 mg/ml to about 355 mg/ml.

In yet other embodiments, methods for producing lytic agents and/or compositions in accordance with the present disclosure include combining a solution of sodium chloride at a concentration from about 0.09% to about 2% by weight of the solution with guanidine hydrochloride, wherein the guanidine hydrochloride is present in the carrier composition in amounts from about 59 mg/ml to about 355 mg/ml.

Embodiments can include one or more of the following advantages.

Previous lytic agents, such as tissue plasminogen activator (tPA), may be effective in lysing acute, blood-based clots possessing fibrin, but are not effective in lysing chronic, collagen-based clots. The lytic agents of the present disclosure are effective in the removal of both acute, blood-based clots, as well as chronic, collagen-based clots. Use of the lytic agents of the present disclosure, optionally in combination with other chemical and/or mechanical treatments, may enhance the lytic effect on both acute and chronic clots, and may also ensure the entire clot is removed from the vasculature, rather than just a portion thereof.

BRIEF DESCRIPTION OF THE DRAWINGS

Various embodiments of the present disclosure will be described herein with references to the accompanying drawings, wherein.

DETAILED DESCRIPTION OF THE EMBODIMENTS

Figure 1:
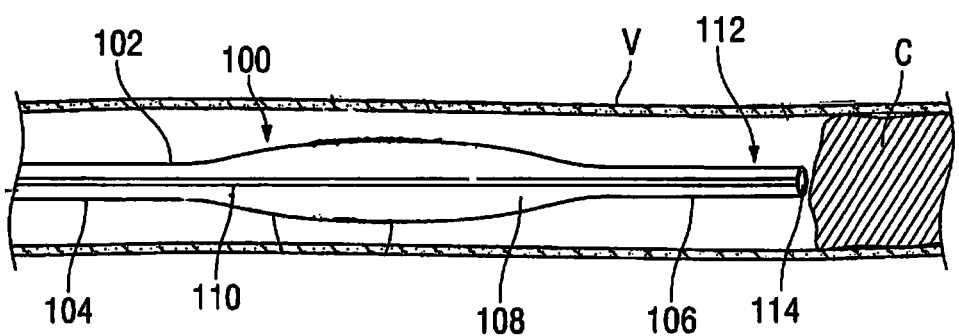
FIG. 1 illustrates an embodiment of the present disclosure of a catheter assembly for use in administering a lytic agent to a blood clot.

Various exemplary embodiments of the present disclosure are discussed hereinbelow in terms of agents suitable for treating clots in the vasculature, especially chronic clots.

In the following discussion, the term "patient" should be understood as referring to a human subject or other animal, and the term "clinician" should be understood as referring to a doctor, nurse, or other care provider and may include support personnel.

The following discussion includes a description of embodiments of the presently disclosed agents for treating clots, especially chronic clots, as well as a description of exemplary corresponding methods of use in accordance with the principles of the present disclosure. In accordance with the present disclosure, an "acute clot," also referred to as a "blood clot," refers to a coagulum in the bloodstream formed of an aggregation of blood factors, mainly platelets, and fibrin with entrapment of cellular elements. Acute clots are often formed due to injury, thromboembolic diseases, and/or stasis. As noted above, acute clots are generally present for a period of time of less than about 14 days. A "chronic clot," as used herein, refers to clots that are present for longer periods of time within the vasculature, greater than about 14 days, and are formed of collagen and fibrin. Both chronic and acute clots can lead to a blockage, or thrombosis, of a blood vessel. In some cases, patients having chronic venous blockages, including DVT, may possess clots that have recannulated, allowing blood flow through the vein.

In accordance with the present disclosure, lytic agents are provided capable of treating chronic clots in vivo. In embodiments, suitable agents include guanidine compounds, such as guanidine hydrochloride, guanidine thiocyanate, guanidine isocyanate, tetramethylguanidinium iodide, combinations thereof, and the like. The lytic agent may slow clot formation, enhance clot dissolution, and/or combinations thereof.

In embodiments, the guanidine compound may be introduced into the vasculature of a patient in a carrier composition, which may be a solution, suspension, and/or emulsion. Suitable carrier compositions include medically acceptable solvents, salt solutions, buffers, combinations thereof, and the like. Carrier compositions include, for example, water, salt solutions including Hanks' Balanced Salt Solution, sodium chloride (saline) solutions, Phosphate Buffered Saline, Dulbecco's Modified Eagle's Medium, phosphate buffers, borate buffers, including sodium borate buffers, BisTris propane buffers (also referred to herein, in embodiments, as BisTris buffers and/or 1,3-Bis-[tris-(hydroxymethyl)-methyl-amino]-propane buffers, combinations thereof, and the like.

The guanidine compound is present in the carrier in a therapeutically effective amount, capable of slowing clot formation and/or enhancing clot dissolution. In embodiments, lytic agents of the present disclosure may include guanidine compounds present in the carrier composition at a molar concentration from about 0.5 M to about 6 M, in embodiments from about 2 M to about 5 M.

In embodiments, the guanidine compound may be present in the carrier composition in amounts from about 59 mg/ml to about 355 mg/ml, in embodiments from about 118 mg/ml to about 295 mg/ml.

In embodiments, a salt solution, such as a sodium chloride solution, may be used as the carrier. The salt may be present in the solution at a concentration from about 0.09% to about 2% by weight, in embodiments from about 0.1% to about 1.4% by weight, in embodiments about 0.9% by weight.

Methods for combining the guanidine compound with the carrier composition are within the purview of one skilled in the art and include, but are not limited to, shaking, stirring, mixing, blending, sonication, combinations thereof, and the like.

In embodiments, the guanidine compound and carrier may be combined by shaking at from about 120 revolutions per minute (rpm) to about 200 rpm, in embodiments from about 140 rpm to about 180 rpm, in embodiments about 160 rpm, for a period of time from about 0.5 hours to about 5 hours, in embodiments from about 1 hour to about 3 hours.

Once formed, the lytic agent including the carrier composition and the guanidine compound may be administered to a patient utilizing conventional means. Such methods include, for example, the use of hypodermic needles, catheters, including infusion catheters, thrombectomy devices, atherectomy devices, combinations thereof, and the like.

Referring now to the figures, wherein like components are designated by like reference numerals throughout the several views, FIG. 1 illustrates one embodiment of a catheter assembly for use in administering a lytic agent such as a guanidine compound to a blood clot "C". The catheter 100 includes an elongate tubular body 102 having a proximal region 104 and a distal region 106. The elongate tubular body 102 of the catheter 100 defines an internal lumen 108 that may be configured and dimensioned to slidably receive a guidewire 110 and having a tip 114 to allow for the passage of fluids therethrough.

In embodiments, suitable catheters which may be utilized for administration of the guanidine compound include, for example, PALINDROME™ catheters, MAHURKAR® catheters, and/or MAHURKAR® MAXID™ catheters, each of which is made available by Covidien, which maintains a principal place of business at 15 Hampshire Street, Mansfield, Mass. Other devices for administration of the guanidine compound include the TRELLIS™ Peripheral Infusion System available from Covidien, infusion catheters such as the CRAGG-MCNAMARA® Valved Infusion Catheter and the MICROMEWI® Multiple Sidehole Infusion Catheter, both available from Covidien, as well as devices otherwise utilized for plaque removal, including the TURBOHAWK™ Peripheral Plaque Excision System and the SilverHawk™ Plaque Excision System, both also available from Covidien.

Methods for treating clots are also described. In embodiments, the method may include accessing a vessel and treating the clot. Initially, a target vessel containing the blood clot must be accessed. Various techniques may be employed for the insertion of catheters into the body including, but not limited to, the use of guidewires, introduction stylets or obturators, dilator/sheath assemblies, and the like. For example, during such procedures, a hollow needle cannula may be inserted into a target vessel in, for example, the venous system, to create a venotomy (entry) site. Upon positioning the needle cannula within the target vessel, a guidewire is inserted through a proximal end of the needle cannula, into the target vessel, and advanced to a desired location within the target vessel proximate to the blood clot. The needle cannula is then withdrawn, leaving a distal end of the guidewire positioned within the target vessel at the desired location, and a proximal end of the guidewire extending outwardly from the venotomy site. A dilator/sheath assembly may then be threaded over the guidewire and into the vessel through the venotomy site to expand the venotomy site and target vessel to facilitate insertion of a catheter.

With reference again to FIG. 1, the guidewire 110 may be positioned proximate to blood clot "C", whereby the catheter 100 may be advanced within a vascular lumen adjacent to a blood clot "C". The lytic agent may then be introduced into the lumen 108 of the catheter 100. The lytic agent is released from the catheter 114 at the clot "C," whereby it breaks down the clot "C" thereby leading to its removal from the vascular lumen. As noted above, in embodiments the lytic agents of the present disclosure may be used in conjunction with thrombectomy devices or other similar devices to facilitate dissolution or removal of the clots.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

Example 1

Acute clots, formed from ovine blood, were formed and treated with guanidine hydrochloride. Clots were formed following the general procedures set forth in Luo et al., "Creation Of Fibrinogen-Enhanced Experimental Blood Clots To Evaluate Mechanical Thrombectomy Devices For Treatment Of Acute Stroke: An In Vitro Study," J. Vasc. Interv. Radiol. 2012 August; 23(8): 1077-83. Briefly, ovine blood was contacted with about 3μ/ml thrombin and about 25 mM calcium chloride. Additional acute clots were formed where about 40 mg/ml fibrinongen was first added to the ovine blood.

Guanidine chloride at concentrations of 6 M and 12 M in 0.9% sodium chloride were added to the clots, with untreated clots and clots treated with 0.2 mg/ml tPA used as controls.

The clots were subjected to mechanical testing to determine the effects of the guanidine chloride on the hardness of the clot, as well as its elasticity and lytic resistance. Briefly, a Texture Analyzer manufactured by Texture Technologies Corporation, running Exponent Software from Texture Technologies Corporation was used. The Texture Analyzer possessed a 1 mm diameter flat probe. Clot samples having a thickness of about 1 mm were prepared and placed underneath the probe, until the probe was about 3 mm above the sample surface. The Texture Analyzer subjected the sample to a 0.5 mm compression test, and then a 1 mm compression test.

Figure 2:
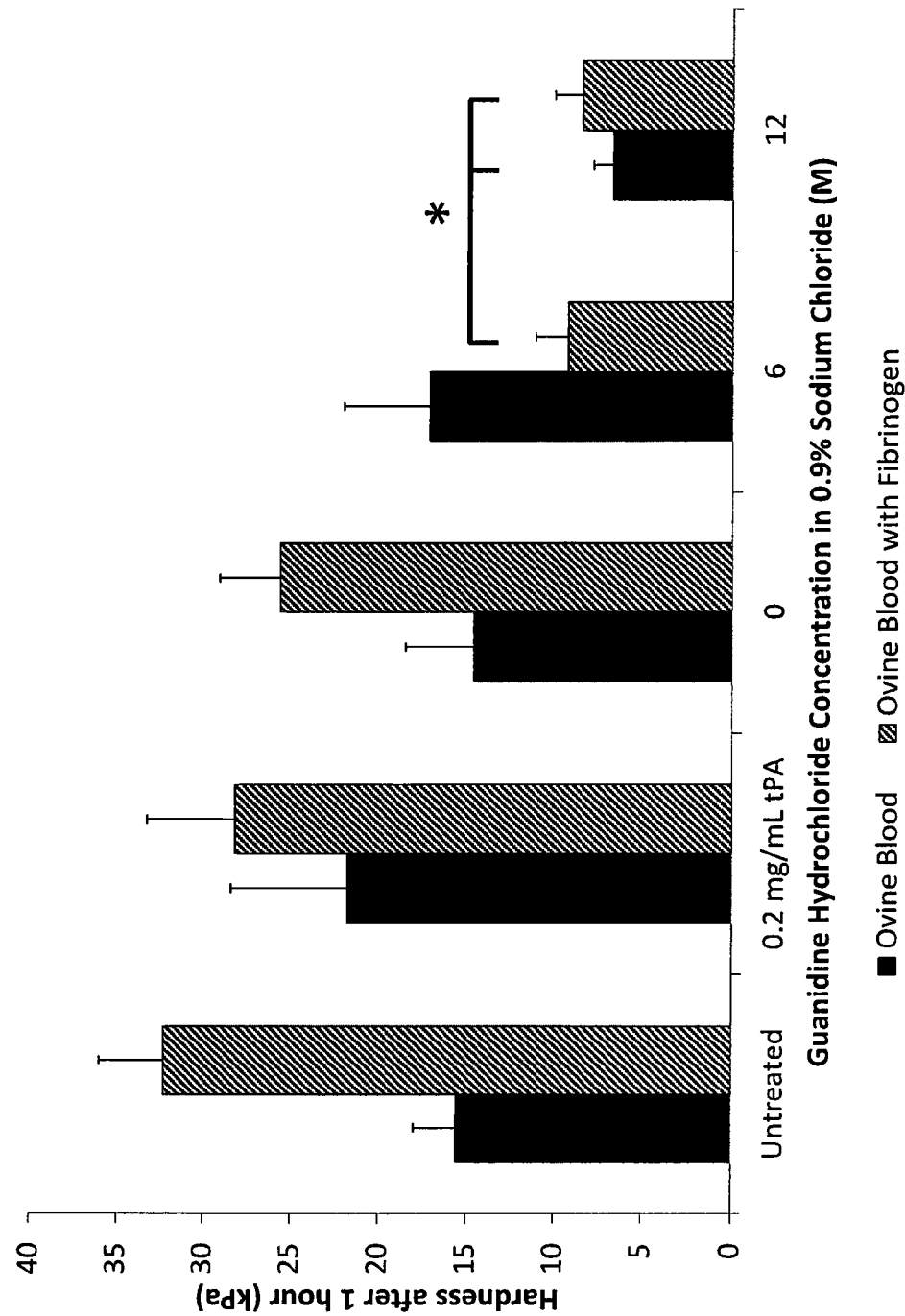
FIG. 2 is a graph depicting the effects of guanidine hydrochloride on the hardness of an acute blood clot, as determined by compression testing.

Measurements were repeated at least 3 times along the length of the sample or every 1 cm. The results of these tests are set forth in FIG. 2. A sample with no guanidine (designated as "0" in FIG. 2) was used as a control.

Before treatment with guanidine hydrochloride, clots prepared without fibrinogen were found to have an elasticity from about 14 kPa to about 20 kPa and a hardness from about 13 kPa to about 18 kPa, while clots prepared with fibrinogen (before treatment with guanidine hydrochloride) were found to have an elasticity from about 40 kPa to about 48 kPa and a hardness from about 28 kPa to about 36 kPa.

After treatment with guanidine hydrochloride, acute clots prepared without fibrinogen were found to have an elasticity from about 4 kPa to about 20 kPa, while acute clots prepared with fibrinogen were found to have an elasticity from about 6 kPa to about 8 kPa. After treatment with guanidine hydrochloride, acute clots prepared without fibrinogen were found to have a hardness from about 7 kPa to about 17 kPa, while acute clots prepared with fibrinogen were found to have a hardness from about 8 kPa to about 9 kPa.

Gravimetric testing to determine lytic resistance of the clots was carried out as follows. Briefly, an incubation shaker was heated to about 37° C. Clots were allowed to rest at a temperature of about 4° C. for 24 hours prior to testing. About 200-300 mg of clot samples were weighed out, with 1 sample placed per well in a 24 well plate. Weights were recorded.

Guanidine hydrochloride solutions were prepared as follows:
1. 12 M Guanidine hydrochloride (GH): 22.93 g GH+20 ml 0.9% sodium chloride
2. 6 M GH: 10 ml 12 M GH+10 ml 0.9% sodium chloride
3. 3 M GH: 10 ml 6 M GH+10 ml 0.9% sodium chloride
4. 1 M GH: 10 ml 3 M GH+20 ml 0.9% sodium chloride
5. 0.75 M GH: 7.5 ml 1 M GH+2.5 ml 10.9% sodium chloride
6. 0.5 M GH: 10 ml 1 M GH+10 ml 0.9% sodium chloride About 1 ml of each solution was placed in each well. The plate was then placed into the incubation shaker and shaken at 160 rpm for 1 hour and 3 hours. The weight was recorded at each time point.

Lytic resistance was defined as follows, as the percent clot remaining:

$$\frac{\text{final weight}}{\text{initial weight}} \times 100$$

After treatment with guanidine hydrochloride, the lytic resistance of the acute clots without fibrinogen was found to be from about 0% to about 30% (% reduction in clot of 100% to 70%), while the lytic resistance of the acute clots with fibrinogen was found to be from about 0% to about 11% (% reduction in clot of 100% to 89%). It was observed that lytic resistance decreased upon increase in the molar concentration of guanidine hydrochloride.

Example 2

Chronic clots, formed of collagen, were formed and treated with guanidine hydrochloride. Chronic collagen clots were formed by reverse dialysis, as generally disclosed in Knight, et al., "In vitro formation by reverse dialysis of collagen gels containing highly oriented arrays of fibrils," J. Biomed. Mater. Res., 41, 185-191 (1998). Briefly, about 1.5 grams collagen was combined with about 45 ml distilled water and 5 ml of 0.5 M acetic acid. A dialysis solution was prepared with 2% polyethylene glycol (PEG) in about 10 mM of a Tris base buffer (2000 ml distilled water added to 40 grams PEG and 2.422 grams Tris Base (also known as Trimethylol Aminomethane, Tris(hydroxymethyl)aminomethane)). The dialysis solution had a pH of about 10. Fibril formation was allowed to proceed over a period of about 48 hours, at which time the collagen was collected and stored in about 10 mM Tris-base solution at a pH of about 7.4 and stored at about 4° C.

Additional chronic clots were prepared by combining collagen gels produced as above, and then adding genipin thereto (about 5 mM genipin solution in about 0.9% sodium chloride).

Figure 3:
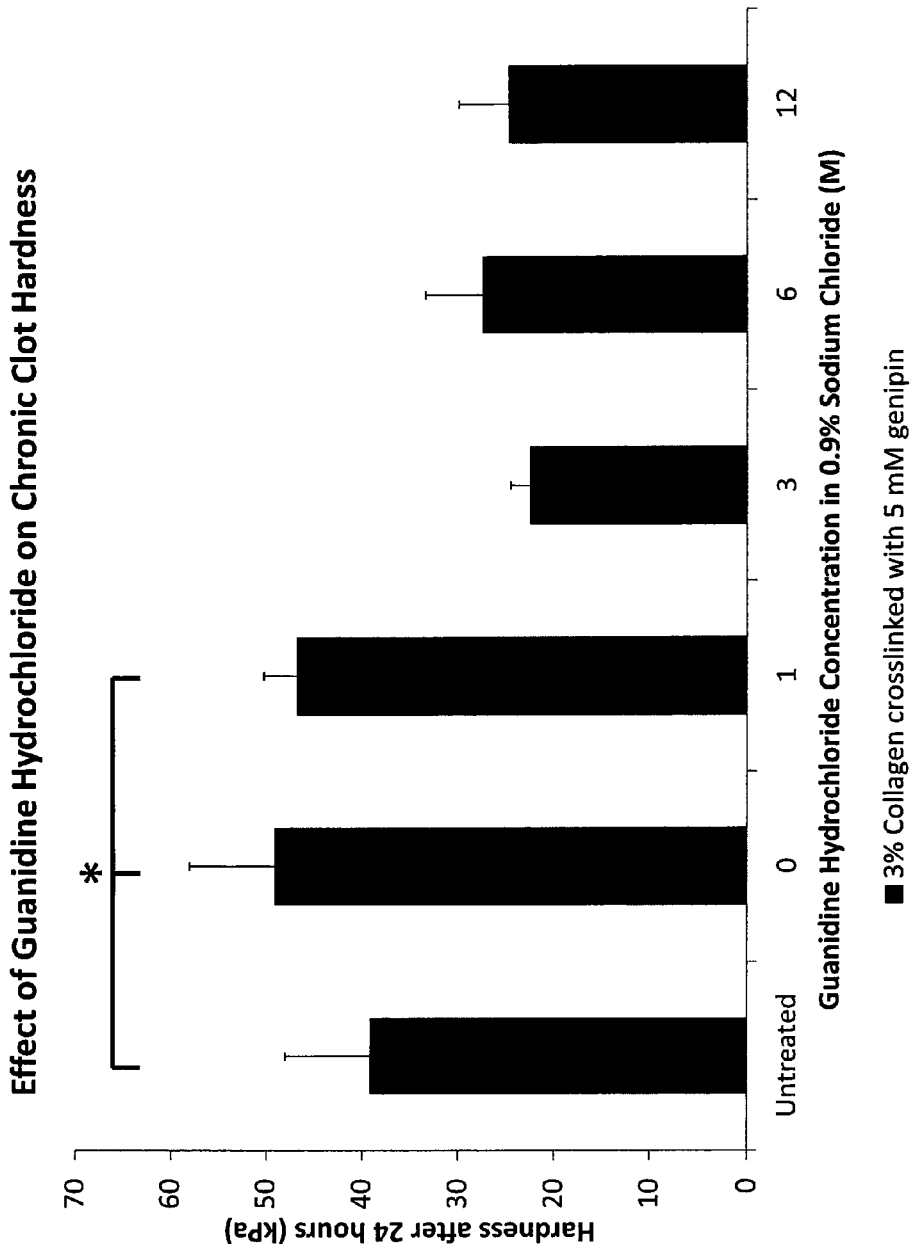
FIG. 3 is a graph depicting the effects of guanidine hydrochloride on the hardness of a chronic collagen clot, as determined by compression testing.

Chronic clots thus formed were subjected to the hardness and gravimetric tests described above in Example 1. The results of the hardness testing are set forth in FIG. 3.

Before treatment with guanidine hydrochloride, clots prepared without genipin were found to have an elasticity from about 38 kPa to about 72 kPa and a hardness from about 16 kPa to about 28 kPa, while clots prepared with genipin (before treatment with guanidine hydrochloride) were found to have an elasticity from about 78 kPa to about 101 kPa and a hardness from about 30 kPa to about 48 kPa.

After treatment with guanidine hydrochloride, chronic clots prepared without genipin were dissolved/broken down to a point where elasticity could not be measured, while chronic clots prepared with genipin were found to have an elasticity from about 30 kPa to about 45 kPa. After treatment with guanidine hydrochloride, chronic clots prepared without genipin were dissolved/broken down to a point where hardness could not be measured, while chronic clots prepared with genipin were found to have a hardness from about 20 kPa to about 30 kPa.

After treatment with guanidine hydrochloride, lytic resistance of the chronic clots without genipin was found to be from about 0% to about 10% (% reduction in clot of 100% to 90%), while lytic resistance of the chronic clots with genipin was found to be from about 50% to about 70% (% reduction in clot of 50% to 30%). It was observed that lytic resistance decreased upon increase in the molar concentration of guanidine hydrochloride.

The results of the gravimetric and mechanical bench top testing on both acute blood and chronic collagen-based clot models, treated with guanidine hydrochloride, may be summarized as follows. Acute blood-based clot models treated with increased concentrations of guanidine hydrochloride did not show a decrease in weight, but exhibited a change in color indicative of a change in the structure of the clot. The mechanical compression testing showed that guanidine hydrochloride had a significant effect on the hardness of the acute blood clot after 1 hour of treatment (see FIG. 2). Thus, using guanidine hydrochloride to treat acute clots with an aspiration catheter and/or thrombectomy device would permit the soft clot to be broken up faster, and more easily aspirated out of the vessel. For chronic collagen-based clots, the guanidine hydrochloride was observed to dissolve most of the collagen clot models after 1 hour, even at low concentrations. In addition, mechanical compression testing showed the guanidine hydrochloride was able to significantly weaken the structure of the chronic collagen clots, as evident by the significant decrease in hardness (see FIG. 3).

The results establish that guanidine hydrochloride is a suitable lytic agent for treatment of all DVTs, from acute to chronic.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the system based on the above-described embodiments. Accordingly, the present disclosure is not to be limited by what has been particularly shown and described, except as indicated by the appended claims.

What is claimed is:

1. An injectable composition comprising:
   a therapeutically effective amount of a lytic agent, wherein the lytic agent comprises:
      at least one guanidine compound; and
      a carrier, wherein the guanidine compound is present in the carrier at a molar concentration from about 0.5 M to about 6 M.

2. The injectable composition of claim 1, wherein the guanidine compound is selected from the group consisting of guanidine hydrochloride, guanidine thiocyanate, guanidine isocyanate, tetramethylguanidinium iodide, and combinations thereof.

3. The injectable composition of claim 1, wherein the carrier is selected from the group consisting of solutions, suspensions, and emulsions.

4. The injectable composition of claim 1, wherein the carrier is selected from the group consisting of medically acceptable solvents, salt solutions, buffers, and combinations thereof.

5. The injectable composition of claim 1, wherein the carrier is selected from the group consisting of water, Hanks' Balanced Salt Solution, sodium chloride solutions, Phosphate Buffered Saline, Dulbecco 1s Modified Eagle1s Medium, phosphate buffers, borate buffers, 1,3-Bis-[tris-(hydroxymethyl)-methyl-amino]-propane buffers, and combinations thereof.

6. The injectable composition of claim 1, wherein the guanidine compound is present in the carrier composition at a molar concentration from about 2 M to about 5 M.

7. The injectable composition of claim 1, wherein the guanidine compound is present in the carrier composition in amounts from about 59 mg/ml to about 355 mg/ml.

8. The injectable composition of claim 1, wherein the carrier comprises a solution of sodium chloride, the sodium chloride present in the solution at a concentration from about 0.09% to about 2% by weight.

9. The injectable composition of claim 1, wherein the therapeutically effective amount of the lytic agent is capable of being administered in vivo to at least one of slow a clot formation or enhance a clot dissolution.

10. The injectable composition of claim 2, wherein the guanidine compound comprises guanidine hydrochloride.

11. A method for treating a clot, the method comprising:
introducing a therapeutically effective amount of a lytic agent to the clot in a vasculature of a patient, wherein the lytic agent comprises:
at least one guanidine compound; and
a carrier, wherein the guanidine compound is present in the carrier at a molar concentration from about 0.5 M to about 6 M.

12. The method of claim 11, wherein the guanidine compound is selected from the group consisting of guanidine hydrochloride, guanidine thiocyanate, guanidine isocyanate, tetramethylguanidinium iodide, and combinations thereof.

13. The method of claim 11, wherein the carrier is selected from the group consisting of solutions, suspensions, and emulsions.

14. The method of claim 11, wherein the carrier is selected from the group consisting of medically acceptable solvents, salt solutions, buffers, and combinations thereof.

15. The method of claim 11, wherein the carrier is selected from the group consisting of water, Hanks' Balanced Salt Solution, sodium chloride solutions, Phosphate Buffered Saline, Dulbecco's Modified Eagle's Medium, phosphate buffers, borate buffers, 1,3-Bis[tris-(hydroxymethyl)-methyl-amino]-propane buffers, and combinations thereof.

16. The method of claim 11, wherein the guanidine compound is present in the carrier composition in amounts from about 59 mg/ml to about 355 mg/ml.

17. The method of claim 11, wherein the carrier comprises a solution of sodium chloride, the sodium chloride present in the solution at a concentration from about 0.09% to about 2% by weight.

18. The method of claim 11, further comprising at least one of slowing formation of the clot or enhancing the dissolution of the clot.

19. The method of claim 12, wherein the guanidine compound comprises guanidine hydrochloride.

20. The method of claim 11, further comprising forming the lytic agent by combining the at least one guanidine compound and the carrier.

* * * * *